(12) United States Patent
Cervenka et al.

(10) Patent No.: US 10,614,458 B2
(45) Date of Patent: Apr. 7, 2020

(54) INFLUENZA VACCINE ADMINISTRATION PAYMENT DEVICE PROCESSING

(75) Inventors: Karen L. Cervenka, Belmont, CA (US); Stacy Pourfallah, Oakland, CA (US); Mary Theresa Taylor, San Francisco, CA (US); Andrew Radlow, Oakland, CA (US)

(73) Assignees: Visa U.S.A. Inc., San Francisco, CA (US); Citicorp Credit Services, Inc., Long Island, NY (US)

( * ) Notice: Subject to any disclaimer, the term of this patent is extended or adjusted under 35 U.S.C. 154(b) by 1003 days.

(21) Appl. No.: 12/855,584

(22) Filed: Aug. 12, 2010

(65) Prior Publication Data
US 2011/0145008 A1 Jun. 16, 2011

Related U.S. Application Data

(60) Provisional application No. 61/234,262, filed on Aug. 14, 2009.

(51) Int. Cl.
*G06Q 20/38* (2012.01)
*G06Q 20/28* (2012.01)
(Continued)

(52) U.S. Cl.
CPC .......... *G06Q 20/385* (2013.01); *G06Q 20/20* (2013.01); *G06Q 20/28* (2013.01); *G06Q 50/22* (2013.01)

(58) Field of Classification Search
CPC ....... G06Q 20/385; G06Q 20/20; G06Q 20/28
(Continued)

(56) References Cited

U.S. PATENT DOCUMENTS

| 4,491,725 A | 1/1985 | Pritchard |
| 5,018,067 A | 5/1991 | Mohlenbrock et al. |

(Continued)

FOREIGN PATENT DOCUMENTS

| AU | 2006203957 | 3/2012 |
| AU | 2006203968 | 3/2012 |

(Continued)

OTHER PUBLICATIONS

"Bartell Drugs launches extensive vaccination program for individuals and business as flu season approaches; Offers Exclusive Pre-Paid FluGram™ Influenza Vaccination Card," available at <http://www.bartelldrugs.com/press/BusinessFluGram.html>.

(Continued)

*Primary Examiner* — Jonathan Durant
(74) *Attorney, Agent, or Firm* — Kilpatrick Townsend & Stockton LLP

(57) ABSTRACT

A payment device has identifiers, read in a magnetic strip or visual indicia by a healthcare provider, for an influenza vaccine and an account issued by an issuer to a party (e.g.; a governmental entity) upon which a transaction can be conducted that is limited to administering the influenza vaccine. The healthcare provider sends an authorization request for the transaction for delivery through its acquirer and a transaction handler to the issuer. The issuer uses the identifiers to authorize the healthcare provider to administer the influenza vaccine and to conduct the transaction, and sends an authorization response to the authorization request back through the transaction handler and the acquirer. After the receiving of the authorization response, the healthcare provider administers the influenza vaccine and conducts the transaction on the account for the sale of the service of the administering of the influenza vaccine.

19 Claims, 6 Drawing Sheets

(51) Int. Cl.
 *G06Q 50/22* (2018.01)
 *G06Q 20/20* (2012.01)
(58) Field of Classification Search
 USPC .......................................................... 705/2, 3
 See application file for complete search history.

(56) References Cited

U.S. PATENT DOCUMENTS

| | | | |
|---|---|---|---|
| 5,070,452 A | 12/1991 | Doyle, Jr. et al. | |
| 5,175,416 A | 12/1992 | Mansvelt et al. | |
| 5,235,507 A | 8/1993 | Sackler et al. | |
| 5,301,105 A | 4/1994 | Cummings, Jr. | |
| 5,324,077 A | 6/1994 | Kessler et al. | |
| 5,335,278 A | 8/1994 | Matchett et al. | |
| 5,550,734 A | 8/1996 | Tarter et al. | |
| 5,628,530 A | 5/1997 | Thornton | |
| 5,644,778 A | 7/1997 | Burks et al. | |
| 5,710,578 A | 1/1998 | Beauregard et al. | |
| 5,832,447 A | 11/1998 | Rieker et al. | |
| 5,832,449 A | 11/1998 | Cunningham | |
| 5,915,241 A | 6/1999 | Giannini | |
| 5,965,860 A | 10/1999 | Oneda | |
| 5,995,939 A | 11/1999 | Berman et al. | |
| 6,012,035 A | 1/2000 | Freeman, Jr. et al. | |
| 6,044,352 A | 3/2000 | Deavers | |
| 6,044,360 A | 3/2000 | Picciallo | |
| 6,082,776 A | 7/2000 | Feinberg | |
| 6,112,183 A | 8/2000 | Swanson et al. | |
| 6,151,588 A | 11/2000 | Tozzoli et al. | |
| 6,208,973 B1 | 3/2001 | Boyer et al. | |
| 6,332,133 B1 | 12/2001 | Takayama | |
| 6,343,271 B1 | 1/2002 | Peterson et al. | |
| 6,401,079 B1 | 6/2002 | Kahn et al. | |
| 6,422,462 B1 | 7/2002 | Cohen | |
| 6,467,684 B2 | 10/2002 | Fite et al. | |
| 6,529,884 B1 | 3/2003 | Jakobsson | |
| 6,615,190 B1 | 9/2003 | Slater | |
| 6,629,081 B1 | 9/2003 | Cornelius et al. | |
| 6,850,901 B1 | 2/2005 | Hunter et al. | |
| 6,877,655 B1 | 4/2005 | Robertson et al. | |
| 6,915,265 B1 | 7/2005 | Johnson | |
| 6,988,075 B1 | 1/2006 | Hacker | |
| 7,072,842 B2 | 7/2006 | Provost et al. | |
| 7,165,049 B2 | 1/2007 | Slater | |
| 7,174,302 B2 | 2/2007 | Patricelli et al. | |
| 7,197,468 B1 | 3/2007 | Patricelli et al. | |
| 7,295,988 B1 | 11/2007 | Reeves | |
| 7,337,949 B2 | 3/2008 | Roth | |
| 7,380,707 B1 | 6/2008 | Fredman | |
| 7,428,494 B2 | 9/2008 | Hasan et al. | |
| 7,566,000 B2 | 7/2009 | Agostino | |
| 7,568,621 B2 | 8/2009 | Von Mueller et al. | |
| 7,650,308 B2 | 1/2010 | Nguyen et al. | |
| 7,680,679 B1 | 3/2010 | Patricelli et al. | |
| 7,752,096 B2 | 7/2010 | Santalo et al. | |
| 7,769,599 B2 | 8/2010 | Yanak et al. | |
| 7,792,688 B2 | 9/2010 | Yanak et al. | |
| 7,810,729 B2 | 10/2010 | Morley, Jr. | |
| 7,866,548 B2 | 1/2011 | Reed et al. | |
| 7,896,248 B2 | 3/2011 | Morley, Jr. | |
| 7,925,518 B2 | 4/2011 | Lee et al. | |
| 7,996,260 B1 | 8/2011 | Cunningham et al. | |
| 8,413,905 B2 | 4/2013 | Pourfallah | |
| 2001/0037295 A1 | 11/2001 | Olsen | |
| 2001/0053986 A1 | 12/2001 | Dick | |
| 2002/0002534 A1 | 1/2002 | Davis et al. | |
| 2002/0002536 A1 | 1/2002 | Braco | |
| 2002/0019808 A1 | 2/2002 | Sharma | |
| 2002/0032583 A1* | 3/2002 | Joao ................... | 705/2 |
| 2002/0055856 A1 | 5/2002 | Adams | |
| 2002/0128863 A1 | 9/2002 | Richmond | |
| 2002/0138309 A1 | 9/2002 | Thomas, Jr. | |
| 2002/0147678 A1 | 10/2002 | Drunsic | |
| 2002/0152180 A1 | 10/2002 | Turgeon | |
| 2002/0169719 A1* | 11/2002 | Dively ................. | G06Q 20/04 705/40 |
| 2002/0198831 A1 | 12/2002 | Patricelli et al. | |
| 2003/0009355 A1 | 1/2003 | Gupta | |
| 2003/0040939 A1 | 2/2003 | Tritch et al. | |
| 2003/0055686 A1 | 3/2003 | Satoh et al. | |
| 2003/0097331 A1 | 5/2003 | Cohen | |
| 2003/0193185 A1 | 10/2003 | Valley et al. | |
| 2003/0200118 A1 | 10/2003 | Lee et al. | |
| 2003/0212642 A1 | 11/2003 | Weller et al. | |
| 2003/0225693 A1 | 12/2003 | Ballard et al. | |
| 2004/0006490 A1 | 1/2004 | Gingrich et al. | |
| 2004/0039693 A1 | 2/2004 | Nauman et al. | |
| 2004/0054935 A1 | 3/2004 | Holvey et al. | |
| 2004/0103000 A1 | 5/2004 | Owurowa et al. | |
| 2004/0111345 A1 | 6/2004 | Chuang et al. | |
| 2004/0128201 A1 | 7/2004 | Ofir et al. | |
| 2004/0138999 A1 | 7/2004 | Friedman et al. | |
| 2004/0148203 A1 | 7/2004 | Whitaker et al. | |
| 2004/0172312 A1 | 9/2004 | Selwanes et al. | |
| 2004/0186746 A1 | 9/2004 | Angst et al. | |
| 2004/0210520 A1 | 10/2004 | Fitzgerald et al. | |
| 2004/0225567 A1 | 11/2004 | Mitchell et al. | |
| 2004/0254816 A1 | 12/2004 | Myers | |
| 2005/0010448 A1 | 1/2005 | Mattera | |
| 2005/0015280 A1 | 1/2005 | Gabel et al. | |
| 2005/0033609 A1 | 2/2005 | Yang | |
| 2005/0038675 A1 | 2/2005 | Siekman et al. | |
| 2005/0065819 A1* | 3/2005 | Schultz ............................. | 705/2 |
| 2005/0065824 A1 | 3/2005 | Kohan | |
| 2005/0071194 A1 | 3/2005 | Bormann et al. | |
| 2005/0119918 A1 | 6/2005 | Berliner | |
| 2005/0182721 A1 | 8/2005 | Weintraub | |
| 2005/0187790 A1 | 8/2005 | Lapsker | |
| 2005/0187794 A1 | 8/2005 | Kimak | |
| 2005/0209893 A1 | 9/2005 | Nahra et al. | |
| 2005/0211764 A1 | 9/2005 | Barcelou | |
| 2005/0246292 A1 | 11/2005 | Sarcanin | |
| 2005/0273387 A1 | 12/2005 | Previdi | |
| 2005/0288964 A1 | 12/2005 | Lutzen et al. | |
| 2006/0010007 A1 | 1/2006 | Denman et al. | |
| 2006/0106645 A1 | 5/2006 | Bergelson et al. | |
| 2006/0106646 A1 | 5/2006 | Squilla et al. | |
| 2006/0111943 A1 | 5/2006 | Wu | |
| 2006/0113376 A1* | 6/2006 | Reed et al. ............. | 235/379 |
| 2006/0129427 A1 | 6/2006 | Wennberg | |
| 2006/0129435 A1 | 6/2006 | Smitherman et al. | |
| 2006/0136270 A1 | 6/2006 | Morgan et al. | |
| 2006/0235761 A1 | 6/2006 | Johnson | |
| 2006/0149529 A1 | 7/2006 | Nguyen et al. | |
| 2006/0149603 A1 | 7/2006 | Patterson et al. | |
| 2006/0149670 A1 | 7/2006 | Nguyen et al. | |
| 2006/0161456 A1 | 7/2006 | Baker et al. | |
| 2006/0173712 A1 | 8/2006 | Joubert | |
| 2006/0184455 A1 | 8/2006 | Meyer et al. | |
| 2006/0167720 A1 | 9/2006 | Harrison et al. | |
| 2006/0206361 A1 | 9/2006 | Logan, Jr. | |
| 2006/0224417 A1 | 10/2006 | Werner | |
| 2006/0229911 A1 | 10/2006 | Gropper et al. | |
| 2007/0005403 A1 | 1/2007 | Kennedy et al. | |
| 2007/0027715 A1 | 2/2007 | Gropper et al. | |
| 2007/0061169 A1 | 3/2007 | Lorsch | |
| 2007/0106607 A1 | 5/2007 | Seib et al. | |
| 2007/0108270 A1 | 5/2007 | Bjoraker et al. | |
| 2007/0125844 A1 | 6/2007 | Libin et al. | |
| 2007/0143215 A1 | 6/2007 | Willems | |
| 2007/0282637 A1 | 12/2007 | Smith | |
| 2008/0010096 A1 | 1/2008 | Patterson et al. | |
| 2008/0071646 A1 | 3/2008 | Hodson et al. | |
| 2008/0133266 A1 | 6/2008 | Allen | |
| 2008/0140447 A1 | 6/2008 | Pourfallah et al. | |
| 2008/0147518 A1 | 6/2008 | Haider et al. | |
| 2008/0177574 A1 | 6/2008 | Gonzalez et al. | |
| 2008/0281733 A1 | 11/2008 | Kubo et al. | |
| 2008/0319794 A1 | 12/2008 | Carlson et al. | |
| 2008/0319904 A1 | 12/2008 | Carlson et al. | |
| 2009/0006203 A1 | 1/2009 | Fordyce, III et al. | |
| 2009/0188983 A1 | 7/2009 | Walker | |
| 2009/0326977 A1 | 12/2009 | Cullen et al. | |

(56) References Cited

U.S. PATENT DOCUMENTS

| | | | |
|---|---|---|---|
| 2010/0010901 | A1 | 1/2010 | Marshall et al. |
| 2010/0010909 | A1 | 1/2010 | Marshall et al. |
| 2010/0057621 | A1 | 3/2010 | Faith et al. |
| 2010/0100484 | A1 | 4/2010 | Nguyen et al. |
| 2010/0145810 | A1 | 6/2010 | Pourfallah et al. |
| 2010/0162171 | A1 | 6/2010 | Felt et al. |
| 2010/0312626 | A1 | 12/2010 | Cervenka |
| 2010/0312631 | A1 | 12/2010 | Cervenka |
| 2010/0312632 | A1 | 12/2010 | Cervenka |
| 2010/0312633 | A1 | 12/2010 | Cervenka |
| 2010/0312634 | A1 | 12/2010 | Cervenka |
| 2010/0312635 | A1 | 12/2010 | Cervenka |
| 2010/0332251 | A1 | 12/2010 | Yanak et al. |
| 2011/0079643 | A1 | 4/2011 | Pourfallah |
| 2011/0082708 | A1 | 4/2011 | Pourfallah |
| 2011/0082739 | A1 | 4/2011 | Pourfallah |
| 2011/0082745 | A1 | 4/2011 | Pourfallah |
| 2011/0106710 | A1 | 5/2011 | Reed et al. |
| 2011/0145008 | A1 | 6/2011 | Cervenka et al. |
| 2011/0166872 | A1 | 7/2011 | Cervenka et al. |
| 2011/0178816 | A1 | 7/2011 | Lee et al. |

FOREIGN PATENT DOCUMENTS

| | | |
|---|---|---|
| CN | 102576452 | 7/2012 |
| EP | 1834275 | 9/2007 |
| EP | 1834314 | 9/2007 |
| EP | 1856663 | 11/2007 |
| EP | 2030163 | 3/2009 |
| EP | 2035990 | 3/2009 |
| EP | 2165297 | 3/2010 |
| EP | 2294540 | 3/2011 |
| EP | 2359324 | 8/2011 |
| EP | 2465091 | 6/2012 |
| HK | 1107164 | 3/2008 |
| HK | 1107172 | 3/2008 |
| HK | 1108752 | 5/2008 |
| JP | 2005124991 A | 5/2005 |
| JP | 2008545210 | 12/2008 |
| JP | 2009541864 | 11/2009 |
| KR | 1020040028017 | 4/2004 |
| KR | 1020050099707 | 10/2005 |
| KR | 1020050094938 | 7/2006 |
| KR | 1020070041183 | 4/2007 |
| WO | 99/22330 | 5/1999 |
| WO | 01/06468 | 1/2001 |
| WO | 03/073353 | 9/2003 |
| WO | 06/074285 A2 | 7/2006 |
| WO | 2011019998 A3 | 4/2011 |
| WO | 2011020039 A3 | 5/2011 |
| ZA | 201000032 | 4/2011 |

OTHER PUBLICATIONS

"Companion Guide 835 Health Care Claim Payment/Advice,"Convansys, Jun. 24, 2004 XP002564865 http://www.njelkids.com/UL/pdf/NJ_835v1_20040820-2.pdf.
"Companion Guide: Health Care Eligibility Benefit Inquiry and Response," Administrative Services of Kansas, ANSI X12N 270/271, pp. 1-18, Aug. 5, 2010.
"FluGram®," US Trademark Registration No. 3,396,025, Registered to Novartis Vaccines and Diagnostics, Inc., Emeryville, CA.
"Give the Gift of Health," US Trademark Registration No. 3,393,037, Registered to Novartis Vaccines and Diagnostics, Inc., Emeryville, CA.
"Givewell Prepaid Healthcare Visa Gift Card—How It Works," available at <www.givewell.com> and <http://www.givewell.com/how-it-works>.
"Novartis Vaccines Launches National Gift-Giving Program to Help Protect Loved Ones by Reserving an Influenza Vaccination," available at <http://www.redorbit.com/modules/news/tools.php?tool=print&id=1088409>.
"Patient Safety Institute: Economic Value of Community Clinical Information Sharing Network, Part 1: Value to Payers (Private, Medicare, Medicaid and Self-Insured Employers) and the Uninsured"; White Paper preapred by Emerging Practices First Consulting Group, 2004, pp. 1-18.
"Press Release: CVS Offers Prepaid Health Cards in Florida Stores," available at <http://www.chaindrugreview.com/front-page/newsbreaks/cvs-offers-prepaid-health-cards-in-florida-stores>.
"Press Release: Winn-Dixie Rolls Out Prepaid Health Insurance Cards," available at <http://www.chaindrugreview.com/front-page/newsbreaks/winndixie-rolls-out-prepaid-health-insurance-cards>.
"Recal Introduces WebSentry Reducing the Risk of Fraud for Internet Transactions; WebSentry Offers System Integrators Cost Effective SET Compliance for E-Commerce"—Canadian Corporation News, May 26, 1999.
"Visa e-Pay" downloaded on www.usa.visa.com/business/accepting_visa/payment_technolgies/epay.html, Feb. 2, 2007, p. 1.
"Visa Introduces Next Generation B2B Payment Service," downloaded on www.corporate.visa.com/md/nr/press136.jsp, Feb. 2, 2007, pp. 1-3.
"Visa Introduces Next Generation B2B Payment Service," downloaded on www.sellitontheweb.com/ezine/news0569.shtml, Feb. 2, 2007, pp. 1-4.
"Visa USA Small Business & Merchants, Visa ePay—Credit counseling Automation," downloaded on www.usa.visa.com/business/accepting_visa/payment_technologies/epay_credit_counseling.html, Feb. 2, 2007, pp. 1-3.
"Visa USA Small Business & Merchants, Visa e-Pay—How it Works" downloaded on www.usa.visa.com/business/accepting_visa/payment_technologies/epay_how it_works.html, Feb. 2, 2007, p. 1.
"Visa USA Small Business & Merchants, Visa epay—Participating Financial Institutes" downloaded on www.usa.visa.com/business/accepting_visa/payment_technolgies/epay_fi.html, at Feb. 2, 2007, p. 1.
"Welcome to American Express Healthpay Plus Works, What is Pay Plus," downloaded on www.152.americanexpress.com/entcampweb/payment_technolgies/epay_how_it_ works.jsp, Feb. 2, 2007, pp. 1-2.
"Welcome to American Express Healthpay Plus(SM)", What is HealthPay Plus downloaded on www.152.americanexpress.com/entcampweb/whatishealthpayplus.jsp at Feb. 2, 2007, pp. 1-5.
Classen, David et al.; "The Patient Safety Institute Demonstration Project: A Model for Implementinga Local Health Information Infrastructure"; 2004, Journal of Healthcare Information Management, vol. 19, No. 4, pp. 75-86.
Hammond, W Edward and Cimino, James "Standards in Medical Informatics: Computer Applications in Health Care and Biomedicine," 2000 Springer, NY XPoo2564866, pp. 225-276.
International Search Report dated Aug. 29, 2008 in PCT/US2008/067460 filed Jun. 19, 2008, 1 page.
International Search Report dated Dec. 20, 2007 in PCT/US2007/71797 filed Jun. 21, 2007, 1 page.
International Search Report dated Feb. 9, 2010 in PCT/US2009/049203 filed Jun. 30, 2009, 3 pages.
International Search Report dated Jun. 28, 2010 in PCT/US2009/066847 filed Dec. 4, 2009, 3 pages.
International Search Report dated May 30, 2008 in PCT/US2007/070780 filed Jun. 8, 2007, 4 pages.
International Search Report dated May 5, 2008 in PCT/US2007/84179 filed Nov. 8, 2007, 1 page.
International Search Report dated Nov. 8, 2007 in PCT/US2006/00274 filed Jan. 4, 2006, 3 pages.
International Search Report dated Nov. 8, 2007 in PCT/US2006/00288 filed Jan. 4, 2006, 3 pages.
International Search Report dated Sep. 29, 2008 in PCT/US2007/74862 filed Jul. 31, 2007, 1 page.
Search Report EIC 3600, dated Aug. 20, 2009 for U.S. Appl. No. 11/230,761.
Supplemental European Search Report dated Jan. 8, 2010 in EP 06717482 filed Jan. 4, 2006, 1 page.
Supplemental European Search Report for EP 08771445.7.
Supplementary European Search Report dated Jan. 8, 2010 in EP 06717481 filed Jan. 4, 2005, 2 pages.

(56) References Cited

OTHER PUBLICATIONS

Supplementary European Search Report dated Mar. 10, 2010 in EP 06717470 filed Jan. 4, 2006, 2 pages.
Supplementary European Search Report dated May 25, 2011 in European Patent Application EP 07798894 filed Jun. 21, 2007, 2 pages.
U.S. Appl. No. 12/643,220, filed Dec. 21, 2009, Patricelli et al. (unpublished).
U.S. Appl. No. 12/854,994, filed Aug. 12, 2010, Cervenka (unpublished).
U.S. Appl. No. 13/329,417, filed Dec. 19, 2007, Cervenka (unpublished).
U.S. Appl. No. 61/234,236, filed Aug. 14, 2009, De Fougerolles (unpublished).
U.S. Appl. No. 61/234,262, filed Aug. 14, 2009, Cervenka et al. (unpublished).
U.S. Appl. No. 61/237,236, filed Aug. 24, 2009, Cervenka et al. (unpublished).

* cited by examiner

INFLUENZA VACCINE ADMINISTRATION PAYMENT DEVICE PROCESSING

CROSS-REFERENCE TO RELATED APPLICATIONS

This application claims priority to, and the benefit of, U.S. Provisional Application Ser. No. 61/234,262, titled "Vaccine Redemption Prepaid Card Through Payment Processing System," filed on Aug. 14, 2009, which is incorporated herein by reference.

FIELD

The present invention relates generally to a prepaid card for a payment processing system, and more particularly to a prepaid or a healthcare service, and most particularly to a prepaid card that identifies an influenza vaccine, where the prepaid card can be used by a patient at a healthcare service provider to obtain an administration of the influenza vaccine, and where the prepaid card is associated with one or more accounts of third parties who are financially response for reimbursing the healthcare service provider for the cost of administering the influenza vaccine to the patient.

BACKGROUND

A vaccine is a biological preparation that improves immunity to a particular disease. A vaccine typically contains a small amount of an agent that resembles a microorganism. The agent stimulates the body's immune system to recognize the agent as foreign, destroy it, and "remember" it, so that the immune system can more easily recognize and destroy any of these microorganisms that it later encounters. Vaccines can be prophylactic (e.g. to prevent or ameliorate the effects of a future infection by any natural or "wild" pathogen), or therapeutic (e.g. vaccines against cancer are also being investigated; see cancer vaccine).

As the drug used in a vaccine is typically a controlled substance regulated by a governmental body, rather the self medicating as an over-the-counter drug, a patient normally must have the vaccine administered a healthcare service provider. The cost of the vaccine, as well as the cost of administering the vaccine to the patient, are typically paid for by an insurance company, where the patient is either the insured or a person for which the patient is financially responsible. After receiving a vaccine, a claims is filed for the insured for the cost of the healthcare goods and services against an insurance policy of the insured. Upon adjudication of the claim, the insurance company pays the healthcare service provider for the cost of the vaccine and the cost of administering the vaccine to the patient.

A patient's vaccine is typically paid for by the patient's insurance company. Substantiation of a healthcare service provided by a healthcare service provider for an insured's insurance policy, and adjudication of the resultant insurance claim for the healthcare service so provided can involve numerous parties that are required to perform numerous functions. Often, these functions must be performed at substantial overhead costs and before the health service provider can be reimbursed for rendering the healthcare service to the patient. In would be an advantage in the relevant arts to provide healthcare service payments to healthcare service providers, such as for vaccine shots, without substantiation or insurance claims system adjudication by a healthcare benefits management entity. Also, there is a need for a system that reduces the costs incurred by healthcare service providers and their patients in the former providing healthcare services to the latter.

SUMMARY

In one implementation, a payment device includes a portable tangible object that has an identifier for an influenza vaccine and an identifier for an account issued to an account holder by an issuer and upon which a transaction can be conducted between a bearer of the payment device and any of a predetermined set of healthcare providers. The account holder to which the issuer issued the account is a governmental entity from whom the bearer receives the payment device, the transaction is limited to the sale of a service of administering the influenza vaccine, and the identifiers are sufficient for a determination by the issuer whether one said healthcare provider is authorized to administer the influenza vaccine and to conduct the transaction on the account for the administration of the influenza vaccine. Means are provided by which the identifiers can be read from the portable tangible object.

In another implementation, a payment device includes a portable tangible object that has an identifier for an influenza vaccine and an identifier for an account issued to an account holder by an issuer and upon which a transaction can be conducted between a bearer of the payment device and any of a predetermined set of healthcare providers. The transaction is limited to the sale of a service of administering the influenza vaccine, and the identifiers are sufficient for a determination by the issuer whether one said healthcare provider is authorized to administer the influenza vaccine and to conduct the transaction on the account for the administration of the influenza vaccine. One of a magnetic strip and visual indicia on a surface of the portable tangible object are provided for the identifiers to read from the portable tangible object.

In yet another implementation, one healthcare provider of a predetermined set of healthcare providers is presented with a payment device that includes a portable tangible object having an identifier for an influenza vaccine and an identifier for an account issued to an account holder by an issuer and upon which a transaction can be conducted between a bearer of the payment device and any of the healthcare providers in the predetermined set. The transaction is limited to the sale of a service of administering the influenza vaccine. The identifiers are sufficient for a determination by the issuer whether the one healthcare provider is authorized to administer the influenza vaccine and to conduct the transaction on the account for the administration of the influenza vaccine. Means are provided by which the identifiers can be read from the portable tangible object. An authorization request, which includes the identifiers, is sent from the one healthcare provider for delivery to the issuer. The authorization request is to conduct the transaction on the account for the sale of the service of the administering of the influenza vaccine. The authorization request is received at the issuer who determines, from the identifiers, that the account is authorized for the transaction on the account for the sale of the service of the administering of the influenza vaccine, and the one healthcare provider is authorized to provide the service of the administering of the influenza vaccine. An authorization response to the authorization request is sent from the issuer for delivery to the one healthcare provide. Upon receipt, at the one healthcare provider, of the authorization response, the one healthcare provider administers the influenza vaccine and conducts the transaction on the account for the sale of the service of the administering of the influenza vaccine.

BRIEF DESCRIPTION OF THE DRAWINGS

Implementations of the invention will become more apparent from the detailed description set forth below when taken in conjunction with the drawings, in which like elements bear like reference numerals.

DETAILED DESCRIPTION

The present discussion considers a prepaid card that can be used by a patient for an influenza (i.e.; 'Flu') vaccine. In various implementations, an issuer would issue an account to an account holder, such as a governmental entity, that would associated with one or more prepaid cards. The account would provide funds, supplied by the account holder, to healthcare providers to reimburse them for providing influenza vaccines to patients who presented a valid influenza vaccine prepaid card. The influenza vaccine prepaid card would be used by patients to obtain a free influenza vaccine from participating healthcare service providers, such as retailers with influenza shot clinics (e.g.; supermarkets, 'big box' stores), doctors, and medical facilities and other such merchants. The influenza vaccine prepaid card can be a plastic magnetic stripe card to facilitate authorization, clearing, and settlement through a typical Point-of-Server terminal (POS) and related systems and processes that such merchants would typically use for other transactions with consumer-account holders who conduct transactions on accounts that are processed by a payment processing network.

Figure 1:
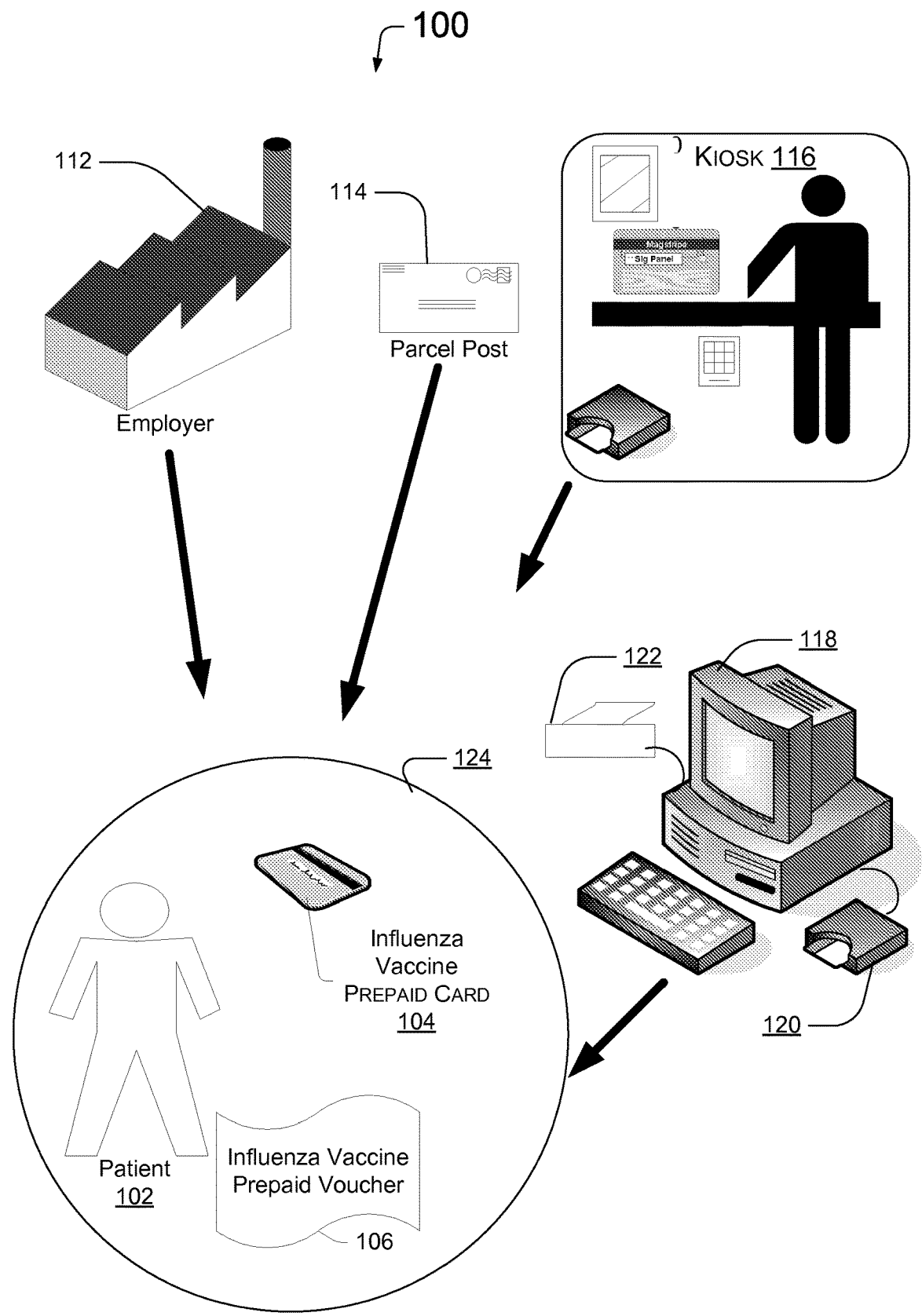
FIG. 1 illustrates an exemplary environment for delivery of prepaid card, or their equivalent, to a patient who is to receive a specific healthcare service to be paid for from an account identified by data encoded on the prepaid card.

FIG. 1 shows examples of who a patient 102 may receive an influenza vaccine prepaid card 104 or an influenza vaccine voucher 106. The influenza vaccine prepaid card 104 can have a magnetic strip from which the identifiers can be read. The identifiers include an identifier for the influenza vaccine and an identifier for the account issued to the account holder by the issuer and upon which a transaction can be conducted between a bearer of the influenza vaccine prepaid card 104 and any healthcare provider in a predetermined set thereof Alternatively, the influenza vaccine voucher 106 may have visual indicia on a surface of thereof from which the identifiers can be read.

The account holder, such as an employer 112 of the patient or one who is financially responsible for the patient 102, may distribute influenza vaccine prepaid cards to its employees. By way of example, the account holder can be a governmental entity who distributes influenza vaccine prepaid cards to subject of the governmental entity. The prepaid card can be ordered from an issuer, or its agents, and received via a postal service 114. A influenza vaccine prepaid card can be obtained by payment to, and operation of, an influenza vaccine prepaid card dispensing kiosk 116. A influenza vaccine paper voucher 106 can be rendered by a printer 122 in communication with a computing apparatus 118 operated by the patient 102, or agent thereof, which voucher has printed on a surface thereof an identifier for an account of a vaccine sponsor. The printed visual indicia rendered with the voucher 106 can be received via the World Wide and/or Internet from the vaccine sponsor or agent thereof.

Figure 2:
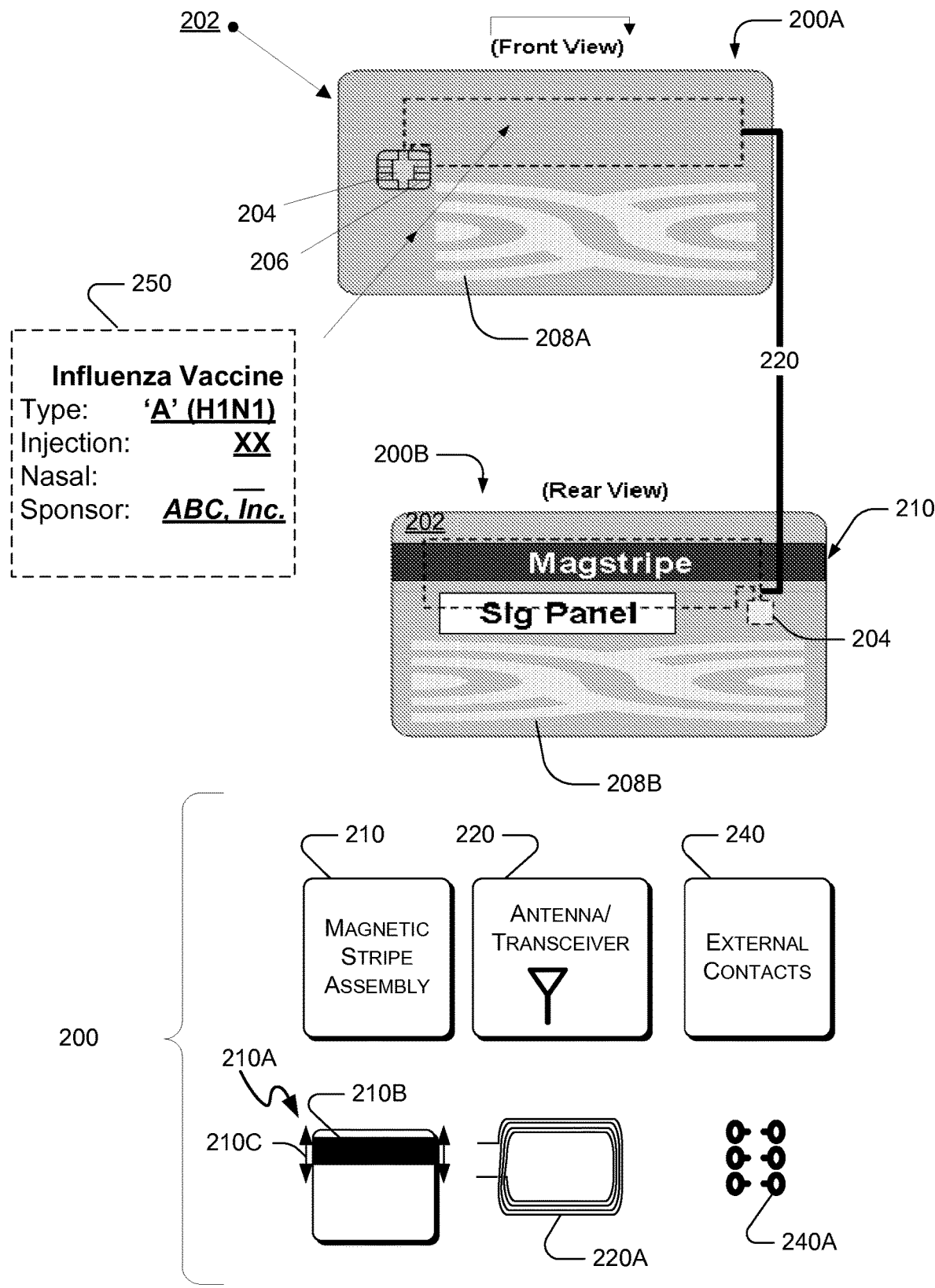
FIG. 2 illustrates possible alternative implementations of a prepaid card.

Turning to FIG. 2, both a front view 200A and a rear view 200B of an exemplary influenza vaccine prepaid card 202 are presented. Images may be displayed on both sides of influenza vaccine prepaid card 202, with image 208A on the front view 200A being either the same as or different from image 208B on the rear view 200B. In this illustration, the front view 200A also displays information about the provider of the influenza vaccine prepaid card.

FIG. 2 also shows exemplary implementations of a data encoding area of influenza vaccine prepaid card 202. The data encoding area may include an optional shielding element, which allows desired electromagnetic, optical, or radiative signals to penetrate while protecting the data encoding area from physical abuse or damage. Flu vaccine prepaid card 202 may optionally have areas outside of the data encoding area shielded from physical abuse or otherwise acceptable forms of electromagnetic radiation. Some of the acceptable signals that are allowed to penetrate the shielding and may include, but are not limited to, signals accompanying a magnetic field, RFID signals, IrDA signals, visible light, invisible light, modulated laser, and/or modulated RF communication signals. By way of example and not limitation, a selective shielding element may comprise a clear plastic shield, conformal coatings, an opaque plastic shield, or a clear thin film, depending on the implementation of the data encoding area.

Non-limiting examples of the data encoding area are shown at reference numeral 200, and include an integrated circuit or 'chip' 204 having contact(s) 206, a magnetic stripe assembly 210, an antenna and/or transceiver 220, and electrical contacts 240. Magnetic stripe assembly 210 may comprise, in the implementation shown as 210A, a reprogrammable magnetic stripe assembly 210B that accepts data and/or commands from a processor and formats and renders that data into a form on a magnetic stripe that is readable by conventional merchant magnetic stripe-reading point of sale (POS) terminals. In this manner, the processor may program a particular account for use in a transaction as a function of user input selecting the account. Alternatively, the processor may erase the magnetic stripe of assembly 210, rendering the card useless in the event of its loss or theft. In the implementation shown as 210A, magnetic stripe assembly 210B at least partially slidably moves 210C into and out of an assembly of influenza vaccine prepaid card 202 (partial view shown), allowing influenza vaccine prepaid card 202 to conduct a transaction at a point of sale terminal that includes a magnetic stripe reader.

Flu vaccine prepaid card 202 can bear, on a surface thereof, an image 250 of various indicia which may identify the specific healthcare service to be provided to the patient by a healthcare service provider to whom the prepaid card is presented. The influenza vaccine prepaid card 202, in some implementation, will not encode data sufficient to identify the patient who is to receive the specific healthcare service. As such the patient can be anonymous to the entities in the payment processing system (e.g., issuer, acquirer and transaction handler) as well as to the healthcare service provider who provides the specific healthcare service to the patient. Despite the privacy of the patient being maintained by implementations disclosed herein, the healthcare service provider can still be reimbursed from an account identified by data on the influenza vaccine prepaid card 202. Also, the identified account encoded on the influenza vaccine prepaid card 202 can correspond to one or more sponsors who are financially responsible to reimburse the healthcare service provider for rendering the specific healthcare service to the patient. As such, the authorization for the cost of the service, and its guaranteed payment to the healthcare service provider, can be provided in real time, without a benefits manager adjudication, without substantiation of the healthcare service against an insurance policy or formulary, and without an insurance claims system process.

Memory, such as may be contained in chip 204, can have encoded therein, but is not limited to; (i) an identifier for the type, kind, manufacturer, wholesaler, of the controlled substance and/or its manner of administration, which may be identified, for instance by Universal Product Code, Stock Keeping Unit, or the other indicia (e.g., UPC, SKU, Bar Code data, etc); (ii) a sponsor who is the account holder for the account from which a healthcare service provider is to be paid of the cost of administering the vaccine to the patient; and (iii) other relevant indicia such as a map and/or location of where an influenza shot can be obtained.

Continuing with FIG. 2, another implementation of the data encoding area is shown as an antenna and/or transceiver 220. Antenna and/or transceiver 220 may include commonly used loop inductors such as the one shown 220A or in those shown in related ISO standards for RF-readable smart cards. With such an interface, account data may be translated, modulated and transmitted in a manner acceptable by an RF contactless merchant POS terminal, a 802.11 WI-FI® or Wi-Max network, or by a cellular or RF communications network. For instance, antenna and/or transceiver 220 may receive a wireless communication from a card read-write device, where the wireless communication carries data for a sponsor's account that is to be written in memory to the data encoding area 200.

Electrical contacts 240 are yet another alternative implementation of the data encoding area shown in FIG. 2. With influenza vaccine prepaid card 202 possessing physical contacts such as an array of conductive pads or shapes 240A, influenza vaccine prepaid card 202 may be placed in physical contact with a merchant's POS terminal, and electrical contacts 240 may establish connectivity to the merchant's financial processing system. The processor may relay account-related information to the merchant's POS terminal through the contact interface, thereby allowing influenza vaccine prepaid card 202 to be utilized with the large number of preexisting merchant POS terminals without hardware and/or software upgrades or changes.

Figure 3:
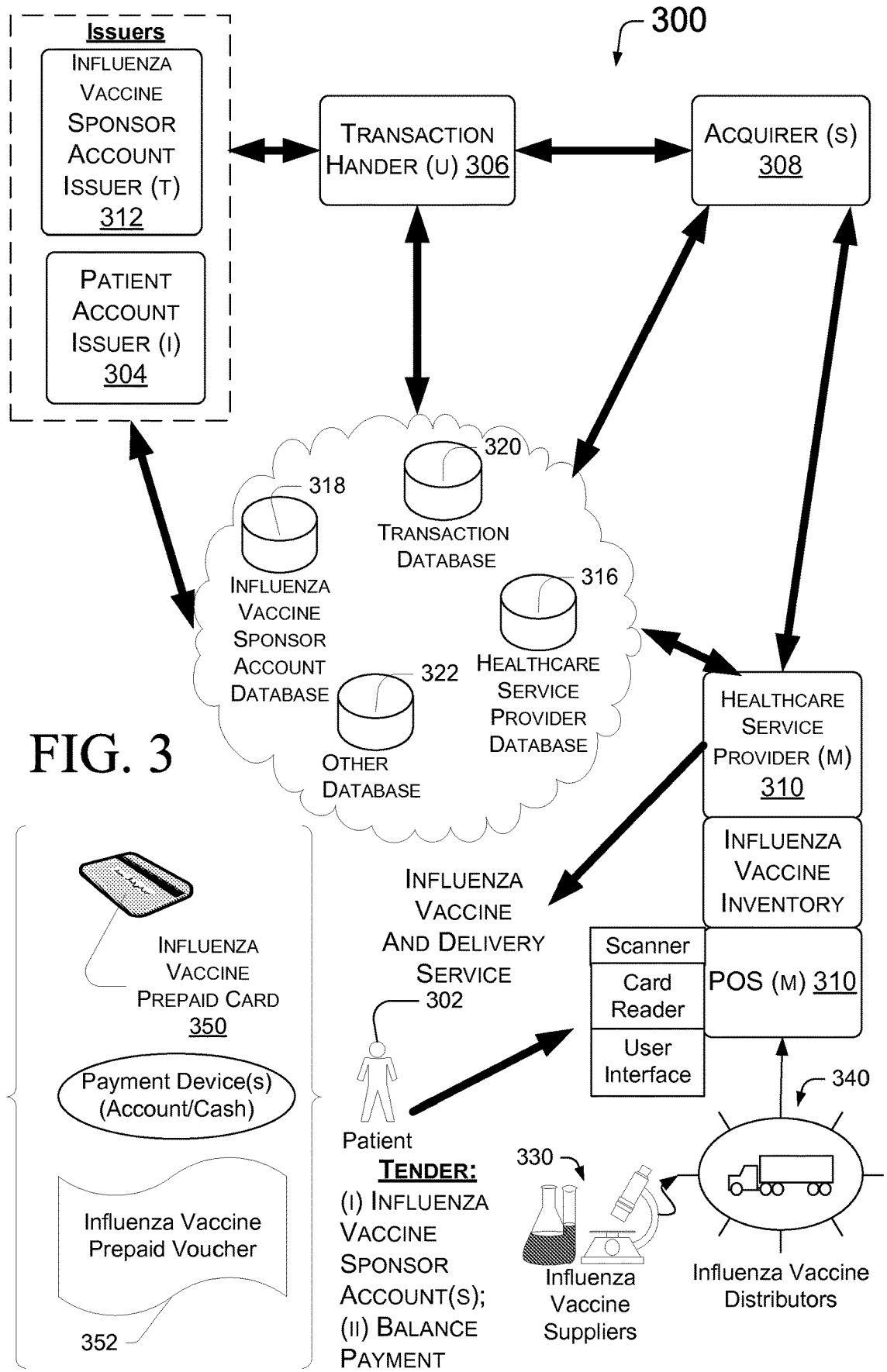
FIG. 3 depicts an environment within a payment processing network seen in FIG. 6 where a prepaid card can be used by a patient to obtain a specific healthcare service to be paid for from an account identified by data encoded on the prepaid card.

Within the exemplary payment processing system depicted in FIG. 6, discussed below, FIG. 3 illustrates the general environment wherein a coupon card, such as coupon card 202 (FIG. 2) obtained by the process described in connection with FIG. 1, is used by a consumer to receive a free, or discounted, influenza shot. To start, one or more vaccine supplier(s) 330 manufacture vaccines for delivery to vaccine distributors 340 who provide vaccine inventory to healthcare service providers 310. Each healthcare service provider (m) 310 has an influenza vaccine inventory and a Point of Service terminal (POS) (m) 310. The POS (m) 310 has a scanner, card reader, and user interface for performing transactions with consumers on accounts issued to the consumer or another to a different account holder such as a sponsor of an influenza vaccine program or campaign.

At POS (m) 310, patient 302 presents to healthcare service provider (m) 310 influenza vaccine prepaid card 350 along with the item(s) patient 302 wishes to purchase. Healthcare service provider (m) 310 uses the card reader associated with POS (m) 310 to read the information stored on influenza vaccine prepaid card 350, including the account identifier associated with one or more sponsors of the vaccine program or campaign. In certain implementations, influenza vaccine prepaid card 350 is read by swiping influenza vaccine prepaid card 350 through POS (m) 310 to read data magnetically encoded in its magnetic stripe. In other implementations, POS (m) 310 reads influenza vaccine prepaid card 350 using a contactless technology, such as RFID, when patient 302 is near POS (m) 310. In yet other implementations, to be read, influenza vaccine prepaid card 350 is inserted into POS (m) 310 such that external contacts on influenza vaccine prepaid card 350 establish connectivity with POS (m) 310. In still other implementations, an influenza vaccine prepaid voucher 352 is scanned by the scanner of POS (m) 310, or visually readable codes thereon are input into POS (m) 310 at the User Interface.

In certain implementations, other information is also read from influenza vaccine prepaid card 350 or voucher 352, such as, by way of example and not limitation, an expiration date, an item type, or an item quantity. In such implementations, POS (m) 310 may determine whether the influenza vaccine prepaid card is valid for a healthcare service requested by patient 302. This may occur, by way of example and not limitation, by comparing the current date with the expiration data of the influenza vaccine prepaid card. Alternatively, POS (m) 310 may determine whether patient 302 has requested the specific influenza vaccine and quantity specified by data on the card.

In one implementation, patient 302 additionally provides influenza vaccine prepaid voucher 352 to healthcare service provider (m) 310. Flu vaccine prepaid voucher 352 has a bar code printed thereon that identifies the influenza vaccine (e.g., the type, kind, quantity, etc., of the influenza vaccine) for which the sponsor's account can be use for payment to the healthcare service provider for the influenza vaccine administered to the patient. In such an implementation, the bar code is scanned with a scanner associated with POS (m) 310 to identify the specific vaccine.

In certain implementations, healthcare service provider (m) 310 may additionally enter the cost of providing the vaccine to the patient into POS (m) 310. In such implementations, the amount may also be printed on influenza vaccine prepaid voucher 352 (e.g.; as a maximum authorized amount). In other implementations, the amount is read by POS (m) 310 from influenza vaccine prepaid card 350 (e.g.; as a maximum authorized amount). In certain implementations, POS (m) 310 calculates the maximum authorized amount for the specific vaccine. This may occur, by way of example and not limitation, where the cost is valid when the patient is also making other purchases from the healthcare service provider (m) 310.

Upon receipt of influenza vaccine prepaid card 350, the transaction is processed similarly to a method described below in connection with an environment 600 depicted in FIG. 6. Healthcare service provider (m) 310 submits an authorization request to its acquirer (s) 308 via POS (m) 310, which includes the account identifier read from influenza vaccine prepaid card 350.

In certain implementations, the authorization request may additionally include an account identifier associated with patient 302 where patient 302 has paid an additional amount for the vaccine and/or for still other items by use of the patient's credit card, debit card, or other portable consumer payment device.

Where acquirer (s) 308 is not the same entity as influenza sponsor account issuer (t) 312, acquirer (s) 308 forwards the transaction information to a transaction handler (u) 306, who in turn forwards it to influenza sponsor account issuer (t) 312 to verify that the account associated with influenza vaccine sponsor account issuer (t) 312 contains sufficient funds to reimburse healthcare service provider (m) 310 for the specific healthcare service to be provided to the patient 302. Of course, if the patient 302 is also making other payments using other accounts, other authorization requests are send to the corresponding patent account issuer (i) 304 of the patent account.

Upon receipt of a reply from influenza sponsor account issuer (t) 312 (i.e.; an authorization response), transaction handler (u) 306 forwards the authorization response to acquirer (s) 308, who forwards it to POS (m) 310 of healthcare service provider (m) 310. Where the authorization response contains an approval of the use of the influenza vaccine prepaid card, patient 302 can receive the specifically identified influenza short service from the healthcare service provider (m) 310 either without cost or at a discount with the balance of the cost being tendered by the patient 302.

In certain implementations, the issuer sends the authorization response to authorize the transaction on the account when the account has an insufficient balance. As such, an amount for the transaction will be collected by the issuer from a third party (e.g.; a governmental entity to whom the account was issued by the issuer) after the transaction has been conducted between the bearer of the payment device and the one healthcare provider.

In other implementations, healthcare service provider (m) 310 invalidates or deletes the influenza vaccine prepaid card(s) stored on influenza vaccine prepaid card 350 using POS (m) 310 once the discount has been applied. In still other implementations, influenza vaccine prepaid card 350 (and voucher 352) may be a one-time use card. In such implementations, healthcare service provider (m) 310 may forgo returning influenza vaccine prepaid card 350 to patient 302. In still other implementations, influenza vaccine prepaid card 350 may be used to store subsequent influenza vaccine credits or service entitlements and therefore is returned to patient 302.

In certain implementations, approval of the transaction for the influenza vaccine administration service may be more involved. In such implementations, the authorization request includes additional information, by way of example and not limitation, the item, the item type, and/or the sponsor of the influenza vaccine prepaid card. In certain implementations this information is forwarded by transaction handler (u) 306 to a third party (not shown) for authentication and/or other processing. In one implementation, healthcare service provider database 316 may be used, by way of example and not limitation, to verify that influenza vaccine sponsor account issuer (t) 312 has issued the influenza vaccine prepaid card 350 being uses by the patient 302. In such an implementation, the authorization process may include a comparison, performed by the third party (not shown) of the additional information provided against information stored in healthcare service provider database 316. In yet other implementations, a third party (not shown) adds a notation to an identifier for the prepaid card 350 or voucher 352 stored in healthcare service provider database 316 once it has been used by the patient 202, thereby preventing its use more than once. The third party (not shown) may have direct access to healthcare service provider database 316 or may access healthcare service provider database 316 via transaction handler (u) 306.

In other implementations, the third party (not shown), who may be an agent of the influenza vaccine sponsor, uses healthcare service provider database 316 to keep a tally of the influenza vaccine prepaid cards used by patients 302. In such an implementation, this information is used by influenza vaccine sponsor account issuer (t) 312 in deciding future influenza vaccine prepaid cards to issue or for identifying specific patients 202 for targeted advertising. In still other implementations, the additional information includes an identifier for one or more advertisements that are to be, or were, presented to patient 302 at the time that influenza vaccine prepaid card 305 or voucher 352 was used by the patient. In such an implementation, after the information is stored in healthcare service provider database 316 by the third party, influenza vaccine sponsor account issuer (t) 312 may charge another entity a fee for each time the advertisement is shown to the patient 302. Alternatively, influenza vaccine sponsor account issuer (t) 312 may change the advertisement associated with an influenza vaccine prepaid card 350 or voucher 352 after the advertisement has been presented with the influenza vaccine prepaid card 350 or voucher 352 a given number of times.

In other implementations, vaccine sponsor account database 318 is used. As with healthcare service provider database 316, a third party (i.e.; an agent of a vaccine sponsor) may access vaccine sponsor account database 318 directly or via transaction handler (u) 306. Vaccine sponsor account database 318 may contain information regarding the account issued to each vaccine sponsor account issuer (t) 312, where influenza vaccine sponsor account issuer (t) 312 is one of (T) vaccine sponsors. In such implementations, the third party (not shown) uses vaccine sponsor account database 318 to verify that the account identifier read from influenza vaccine prepaid card 350 is associated with one of the 'R' influenza vaccine prepaid card sponsors. Vaccine sponsor account database 318 may additionally be used to verify that the associated account contains funds sufficient to reimburse healthcare service provider (m) 310 for the discount applied. In certain implementations, the aforementioned third party (not shown) is the same entity as transaction handler (u) 306. In other implementations, third party (not shown) is a separate entity from transaction handler (u) 306.

When healthcare service provider (m) 310 submits the transaction to a payment processing system 300 via POS (m) 310 for clearing and settlement, the account of influenza vaccine sponsor account issuer (t) 312 is debited (e.g.; decreased) for the cost of the vaccine. Specifically, healthcare service provider (m) 310 submits a request for payment to acquirer (s) 308. Where acquirer (s) 308 is not the same entity as influenza sponsor account issuer (t) 312, acquirer (s) 308 forwards the request to transaction handler (u) 306. Transaction handler (u) 306 in turn requests payment for the vaccine from influenza sponsor account issuer (t) 312, where influenza sponsor account issuer (t) 312 is the issuer of the account associated with influenza vaccine sponsor. Flu sponsor account issuer (t) 312 debits (decreases) the currency in the account and forward the payment to transaction handler (u) 306 who forwards the payment to acquirer (s) 308. Finally, acquirer (s) 308 credits the account of healthcare service provider (m) 310 with the cost of providing the controlled substance, and its administration, to the patient 302.

In certain implementations, the clearing and settlement process may involve a third party (not shown). In such an implementation, the third party may, by way of example and not limitation, record each influenza vaccine prepaid card 350 or voucher 352 that has been cleared and settled. This record may be kept in healthcare service provider database 316 or in another separate database 322. Alternatively or in addition to, the third party may verify that the influenza vaccine prepaid card 350 or voucher 352 was used in the transaction being cleared and settled. In yet other implementations, the third party may determine the account associated with sponsor of the vaccine in order that transaction handler (u) 306 may request influenza sponsor account issuer (t) 312 to debit (decrease) the currency in the corresponding account of the sponsor. In such implementations, the third party may access vaccine sponsor account database 318.

As will be understood by a person of ordinary skill in the art, the process described in connection with FIG. 3 is equally applicable to the situation where a patient uses a prepaid card having multiple influenza vaccines service payments credited or stored thereon such that the prepaid card is not a single use card but rather can be used for receiving a plurality of influenza shots (e.g.; one influenza shot for each member of an employee's family up to eight (8) influenza shots). In such a situation, the influenza vaccine prepaid cards may be provided by different influenza vaccine prepaid card sponsors having accounts issued by different issuers. For example, card 350 or voucher 352 may show one or more accounts which will attribute the cost of the influenza vaccine to one account and the cost of administering the influenza vaccine controlled substance (i.e., giving the influenza shot) to yet another and different account. Further, it will be clear to a person of ordinary skill in the art that a prepaid influenza vaccine card may have multiple different types of influenza vaccine shot credits stored thereon that are valid at respectively different healthcare service providers, each having a different acquirer.

Figure 4:
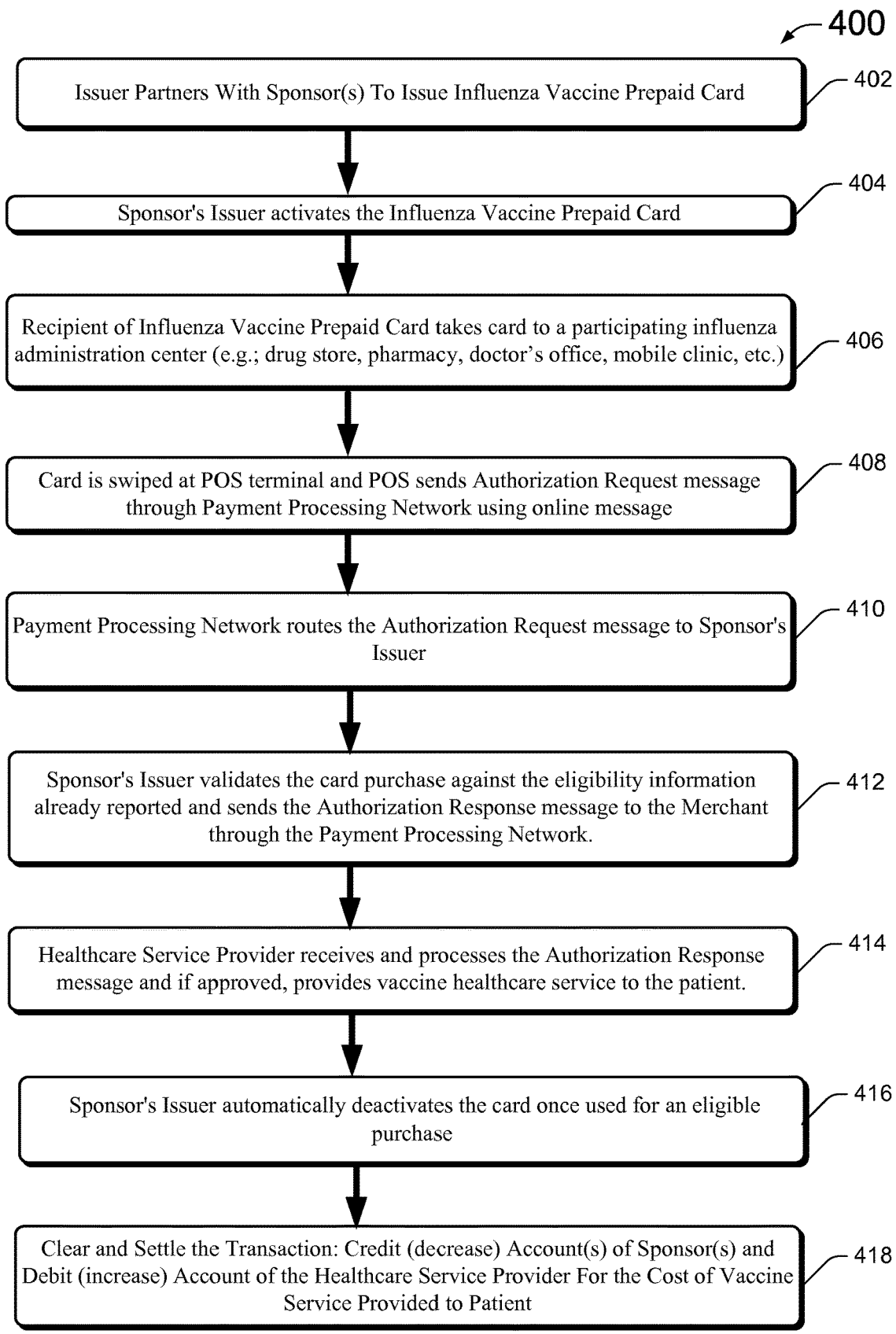
FIG. 4 depicts a flow chart of a first exemplary method in which a prepaid card can be used at a Point of Service terminal for a patient to obtain a specific healthcare service to be paid for from an account identified by data encoded on the prepaid card.

Turning now to FIG. 4, a flow chart of an exemplary method 400 used in a transaction to process an influenza vaccine service cost stored on an influenza vaccine prepaid card is presented. As indicated by block 402, an issuer would partner with businesses, non-profits, and/or government agencies to issue an influenza vaccine prepaid card, where each partner would sponsor the cost of the influenza vaccines, either the cost of the influenza vaccine, the cost of administering the influenza vaccine to patients, or both. The influenza vaccine prepaid card would be used by patients to obtain a free (or discounted) influenza vaccine from participating healthcare service providers, such as retailers with influenza shot clinic, doctors, and medical facilities. Data to facilitate authorization, clearing, and settlement of an influenza vaccine administration could be read from a magnetic strip on an influenza vaccine prepaid card, or could be read from visual indicia on a surface of a voucher. These data could read by a typical merchant POS system and processed as would other consumer purchases that are processed through a payment processing network by a consumer's use of a portable payment device (e.g.; an open loop credit/debit/prepaid card). At block 404, an issuer of an account issued to a sponsor of the influenza vaccine program or campaign would individually, or in bulk, activate the influenza vaccine prepaid card(s). At block 404, a recipient of an influenza vaccine prepaid card takes the card to a participating healthcare provider, which could be a drug store, pharmacy, doctor's office, mobile clinic, etc. The healthcare service provider (i.e., merchant) would have two POS processing options, seen respectively in FIGS. 4-5.

In FIG. 4, product information is captured and eligibility is validated at the POS via an authorization request message sent from the POS. At block 408, the influenza vaccine prepaid card is swiped at the POS terminal and the POS sends an authorization request message through a payment processing network using a standard '0100' online message with a drug product code corresponding to the specific influenza vaccine service designated in Field 104 of the 0100 authorization request message. At block 408, the payment processing network routes the authorization request message to sponsor's issuer, such as via the healthcare provider's acquirer and the transaction handler. At block 412, the influenza vaccine sponsor's issuer validates the purchase eligibility and sends the standard 0100 authorization response message to the healthcare service provider (e.g., the merchant) back through the payment processing network via the healthcare provider's acquirer and the transaction handler. At block 414, the healthcare provider receives and processes the standard 0100 authorization response message and if approved, administers the influenza vaccine to the patient via a shot (or other administration technique such as by nasal inhalation). At block 416, the sponsor's issuer can automatically deactivates the influenza vaccine prepaid card or voucher if it is a one-use-only card or voucher. The healthcare service provider can, in some implementations, automatically receive payment for its vaccine administration services, along with all other payment processing network transactions (e.g.; via clearing and settlement) as shown at block 418.

Figure 5:
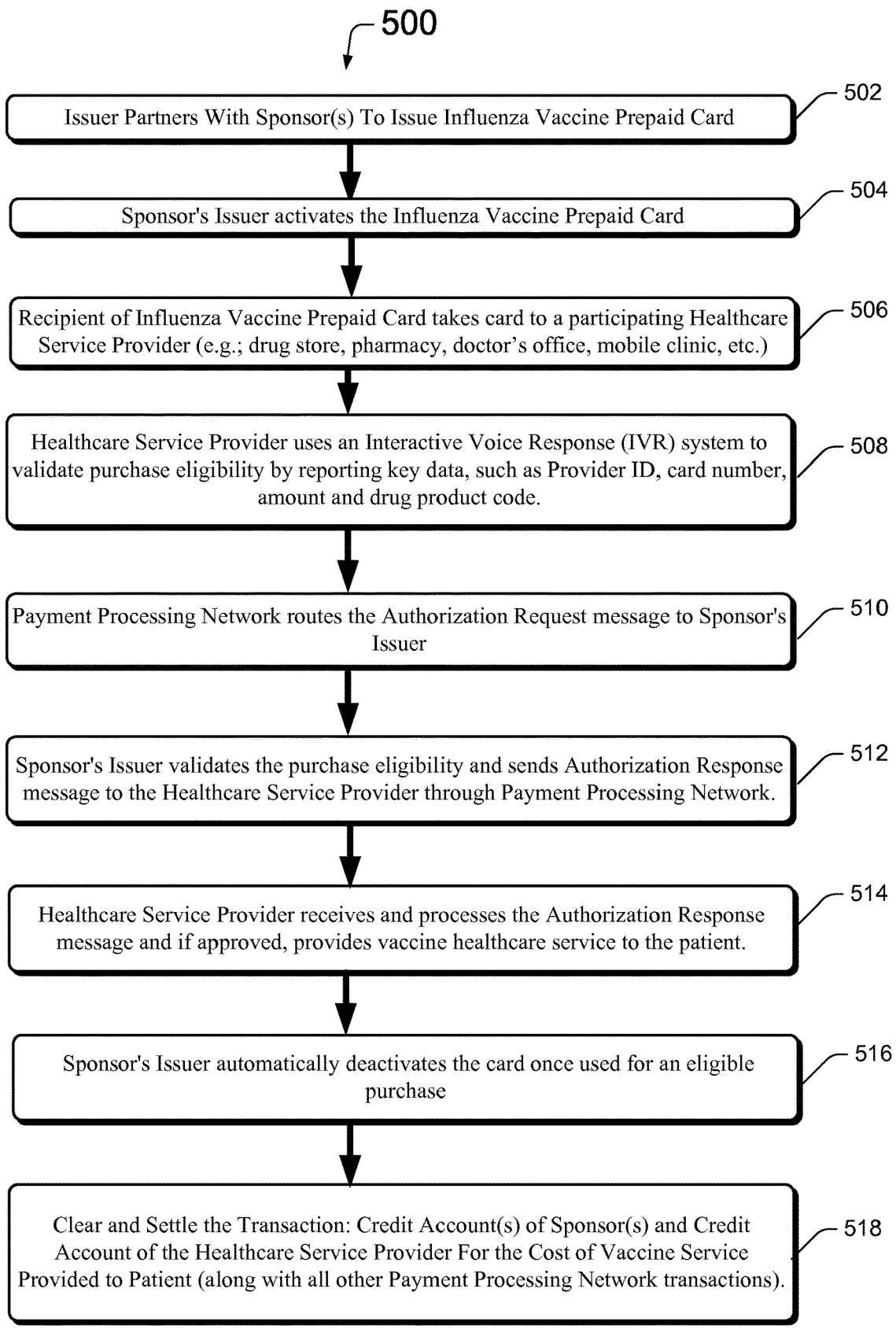
FIG. 5 depicts a flow chart of a second exemplary method for a patient to obtain a specific healthcare service to be paid for from an account corresponding to a prepaid card.

In FIG. 5, block 502-506 are similar to step 402-406 in FIG. 4. In block 508 of FIG. 5, a healthcare service provider, rather than using a POS to read an influenza vaccine prepaid card or voucher, uses an Interactive Voice Response (IVR) system to validate purchase eligibility by reporting key data read from the influenza vaccine prepaid card or voucher, such as Provider ID, card number, amount and drug product code. At block 510, the payment processing network routes the authorization request message to the sponsor's issuer, such as via the healthcare provider's acquirer and the transaction handler. At block 512, the influenza vaccine sponsor's issuer validates the purchase eligibility and sends the standard 0100 authorization response message to the healthcare service provider (e.g., the merchant) back through the payment processing network via the healthcare provider's acquirer and the transaction handler. At block 514, the healthcare provider receives and processes the standard 0100 authorization response message and if approved, provides the patient with the controlled substance (i.e., vaccine) administered via a shot (or other administration such as by nasal inhalation). At block 516, the sponsor's issuer can automatically deactivates the card or voucher, if spent, once used for an eligible purchase. The healthcare service provider can, in some implementations, automatically receive payment for its vaccine services purchases, along with all other payment processing network transactions (e.g.; via clearing and settlement) as shown at block 518.

In some implementation, an influenza vaccine prepaid card can be associated with a sponsor's account number that has a Bank Identification Number (BIN) that is assigned by a transaction handler (e.g., by VISA® Inc. or other transaction handler). For instance, the account number can begin with the digit '4'. In other implementations, the prepaid card can have a form factor of a physical plastic card design that may contain a bar code that conveys the influenza vaccine drug product code. In other implementations, the influenza vaccine service would not be permitted to be combined, by the patient or healthcare service provider, with the purchase of any other good or service. In still other implementations, a private label service for a payment processing network could be used, such as for the influenza vaccine sponsor's issuer or for a specific transaction handler (i.e.; VISA® Inc. VISANET®), who validates that an influenza vaccine prepaid card is being redeemed from an authorized or participating location and/or healthcare service provider (i.e.; merchant), that the funds have been set aside with the sponsor's issuer for the vaccine that has not yet been redeemed, and that the influenza vaccine prepaid card is still valid. The payment processing network clearing and settlement system can be used to move funds between the funding party and the vaccine redemption location (e.g.; the merchant and/or location thereof, administering the influenza shot to the patient).

In certain implementations, individual blocks described above for FIGS. 4-5 may be combined, eliminated, or reordered. Also, in certain implementations, instructions (e.g.; software) are encoded in computer readable medium wherein those instructions are executed by computing apparatus (e.g.; hardware) processor to perform one or more of the blocks for FIGS. 4-5. In yet other implementations, instructions reside in any other computer program product, where those instructions are executed by a computer external to, or internal to, a computing system to perform one or more of the blocks of FIGS. 4-5. In either case the instructions may be encoded in an non-transient computer readable medium comprising, for example, a magnetic information storage medium, an optical information storage medium, an electronic information storage medium, and the like. "Electronic storage media," may mean, for example and without limitation, one or more devices, such as and without limitation, a PROM, EPROM, EEPROM, Flash PROM, compact flash, smart media, and the like.

An Exemplary Transaction Processing System/Payment Processing Network

Figure 6:
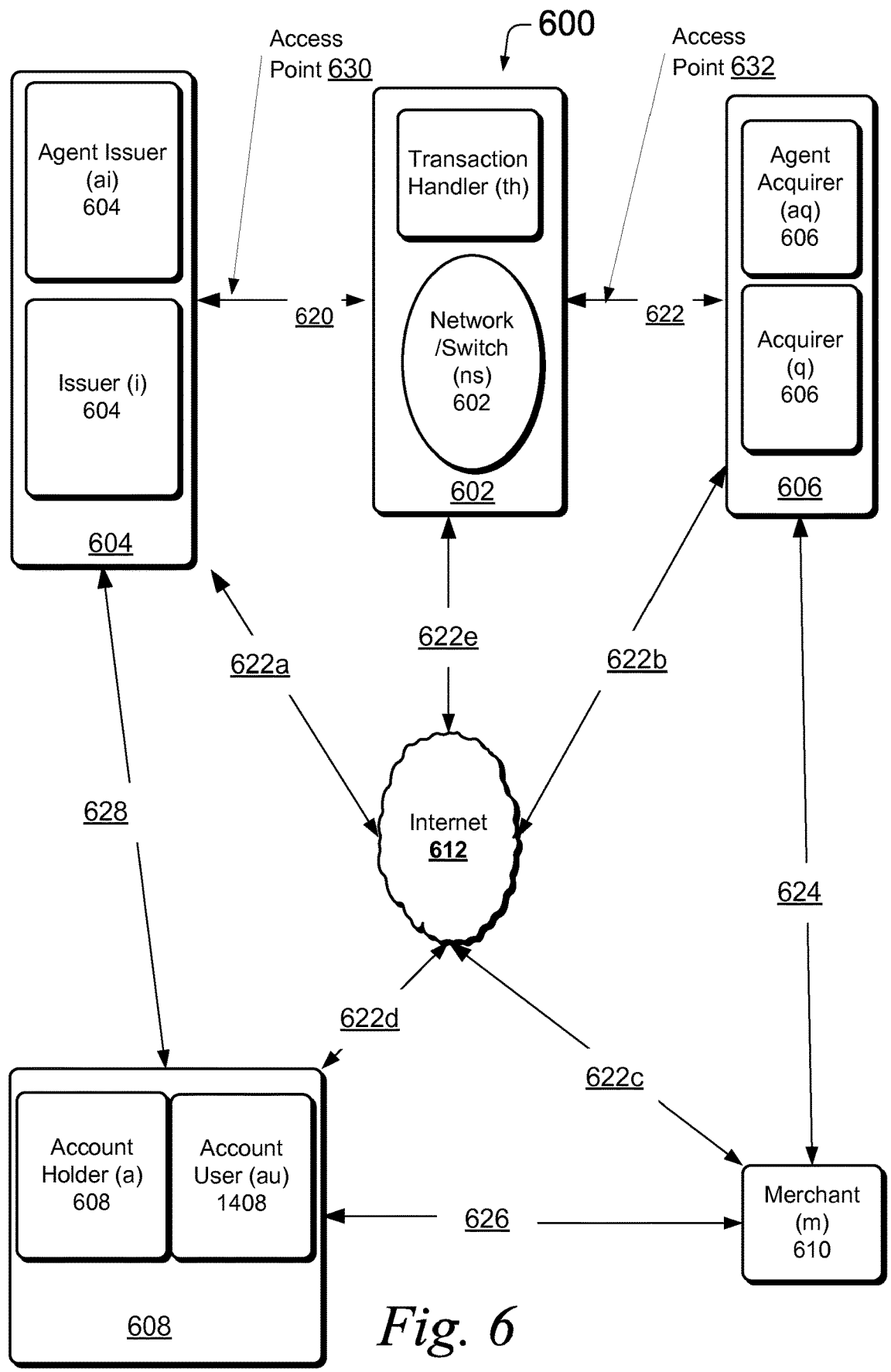
FIG. 6 illustrates an exemplary payment processing network.

Referring to FIG. 6, a transaction processing system 600 is seen to as an environment in which methods 400 and 500 in FIGS. 4-5 can be performed, and as a general example for payment processing system 300 in FIG. 3. Transaction processing system 600 is a telecommunications network that may make use of any suitable telecommunications network and may involve different hardware, different software and/ or different protocols then those discussed below. Transaction processing system 600 is a global telecommunications network that supports purchase and cash transactions using any bankcard, travel and entertainment cards, and other private label and proprietary cards. The network also supports ATM transactions for other networks, transactions using paper checks, transactions using smart cards and transactions using other financial instruments.

These transactions are processed through the network's authorization, clearing and settlement services. Authorization is when an issuer approves or declines a sales transaction before a purchase is finalized or cash is dispersed. Clearing is when a transaction is delivered from an acquirer to an issuer for posting to the customer's account. Settlement is the process of calculating and determining the net financial position of each member for all transactions that are cleared. The actual exchange of funds is a separate process.

Transactions can be authorized, cleared and settled as either a dual message or a single message transaction. A dual message transaction is sent twice-the first time with only information needed for an authorization decision, an again later with additional information for clearing and settlement. A single message transaction is sent once for authorization and contains clearing and settlement information as well. Typically, authorization, clearing and settlement all occur on-line.

The general environment of FIG. 6 include that of a merchant (m) 610, such as the merchant, who can conduct a transaction for goods and/or services with an account user (au) (e.g., consumer) on an account issued to an account holder (a) 608 by an issuer (i) 604, where the processes of paying and being paid for the transaction are coordinated by at least one transaction handler (th) 602 (e.g., the transaction handler) (collectively "users"). The transaction includes participation from different entities that are each a component of the transaction processing system 600.

The transaction processing system 600 may have at least one of a plurality of transaction handlers (th) 602 that includes transaction handler (1) 602 through transaction handler (TH) 602, where TH can be up to and greater than an eight digit integer.

The transaction processing system 600 has a plurality of merchants (m) 610 that includes merchant (1) 610 through merchant (M) 610, where M can be up to and greater than an eight digit integer. Merchant (m) 610 may be a person or entity that sells goods and/or services. Merchant (m) 610 may also be, for instance, a healthcare service provider who can administer a controlled substance (e.g.; a drug) to a patient in the form of a vaccine, such as influenza shot or a nasal inhalation procedure. In a business-to-business setting, the account holder (a) 608 may be a second merchant (m) 610 making a purchase from another merchant (m) 610.

Transaction processing system 600 includes account user (1) 608 through account user (AU) 608, where AU can be as large as a ten digit integer or larger. Each account user (au) conducts a transaction with merchant (m) 610 for goods and/or services using the account that has been issued by an issuer (i) 604 to a corresponding account holder (a) 608. Data from the transaction on the account is collected by the merchant (m) 610 and forwarded to a corresponding acquirer (a) 606. Acquirer (a) 606 forwards the data to transaction handler (th) 602 who facilitates payment for the transaction from the account issued by the issuer (i) 604 to account holder (a) 608.

Transaction processing system 600 has a plurality of acquirers (q) 606. Each acquirer (q) 606 may be assisted in processing one or more transactions by a corresponding agent acquirer (aq) 606, where 'q' can be an integer from 1 to Q, where aq can be an integer from 1 to AQ, and where Q and AQ can be as large as a eight digit integer or larger. Each acquirer (q) 606 may be assisted in processing one or more transactions by a corresponding agent acquirer (aq) 606, where 'q' can be an integer from 1 to Q, where aq can be an integer from 1 to AQ, and where Q and AQ can be as large as a eight digit integer or larger.

The transaction handler (th) 602 may process a plurality of transactions within the transaction processing system 600. The transaction handler (th) 602 can include one or a plurality or networks and switches (ns) 602. Each network/ switch (ns) 602 can be a mainframe computer in a geographic location different than each other network/switch (ns) 602, where 'ns' is an integer from one to NS, and where NS can be as large as a four digit integer or larger.

Dedicated communication systems 620, 622 (e.g., private communication network(s)) facilitate communication between the transaction handler (th) 602 and each issuer (i) 604 and each acquirer (a) 606. A Network 612, via e-mail, the World Wide Web, cellular telephony, and/or other optionally public and private communications systems, can facilitate communications 622a-622e among and between each issuer (i) 604, each acquirer (a) 606, each merchant (m) 610, each account holder (a) 608, and the transaction handler (th) 602. Alternatively and optionally, one or more dedicated communication systems 624, 626, and 628 can facilitate respective communications between each acquirer (a) 606 and each merchant (m) 610, each merchant (m) and each account holder (a) 608, and each account holder (a) 608 and each issuer (i) 604, respectively.

The Network 612 may represent any of a variety of suitable means for exchanging data, such as: an Internet, an intranet, an extranet, a wide area network (WAN), a local area network (LAN), a virtual private network, a satellite communications network, an Automatic Teller Machine (ATM) network, an interactive television network, or any combination of the forgoing. Network 612 may contain either or both wired and wireless connections for the transmission of signals including electrical, magnetic, and a combination thereof. Examples of such connections are known in the art and include: radio frequency connections, optical connections, etc. To illustrate, the connection for the transmission of signals may be a telephone link, a Digital Subscriber Line, or cable link. Moreover, network 612 may utilize any of a variety of communication protocols, such as Transmission Control Protocol/Internet Protocol (TCP/IP), for example. There may be multiple nodes within the network 612, each of which may conduct some level of processing on the data transmitted within the transaction processing system 600.

Users of the transaction processing system 600 may interact with one another or receive data about one another within the transaction processing system 600 using any of a variety of communication devices. The communication device may have a processing unit operatively connected to a display and memory such as Random Access Memory ("RAM") and/or Read-Only Memory ("ROM"). The communication device may be combination of hardware and software that enables an input device such as a keyboard, a mouse, a stylus and touch screen, or the like.

For example, use of the transaction processing system 600 by the account holder (a) 608 may include the use of a portable consumer device (PCD). The PCD may be one of the communication devices, or may be used in conjunction with, or as part of, the communication device. The PCD may be in a form factor that can be: a card (e.g., bank card, payment card, financial card, credit card, charge card, debit card, gift card, transit pass, smart card, access card, a payroll card, security card, healthcare card, or telephone card), a tag, a wristwatch, wrist band, a key ring, a fob (e.g., SPEED-PASS® commercially available from ExxonMobil Corporation), a machine readable medium containing account information, a pager, a cellular telephone, a personal digital assistant, a digital audio player, a computer (e.g., laptop computer), a set-top box, a portable workstation, a mini-computer, or a combination thereof. The PCD may have near field or far field communication capabilities (e.g., satellite communication or communication to cell sites of a cellular network) for telephony or data transfer such as communication with a global positioning system (GPS). The PCD may support a number of services such as SMS for text messaging and Multimedia Messaging Service (MMS) for transfer of photographs and videos, electronic mail (email) access.

The PCD may include a computer readable medium. The computer readable medium, such as a magnetic stripe or a memory of a chip or a chipset, may include a volatile, a non-volatile, a read only, or a programmable memory that stores data, such as an account identifier, a consumer identifier, and/or an expiration date. The computer readable medium may including executable instructions that, when executed by a computer, the computer will perform a method. For example, the computer readable memory may include information such as the account number or an account holder (a) 608's name.

Examples of the PCD with memory and executable instructions include: a smart card, a personal digital assistant, a digital audio player, a cellular telephone, a personal computer, or a combination thereof. To illustrate, the PCD may be a financial card that can be used by a consumer to conduct a contactless transaction with a merchant, where the financial card includes a microprocessor, a programmable memory, and a transponder (e.g., transmitter or receiver). The financial card can have near field communication capabilities, such as by one or more radio frequency communications such as are used in a BLUETOOTH® communication wireless protocol for exchanging data over short distances from fixed and mobile devices, thereby creating personal area networks.

Merchant (m) 610 may utilize at least one POI terminal (e.g., Point of Service or browser enabled consumer cellular telephone); that can communicate with the account user (au) 608, the acquirer (a) 606, the transaction handler (th) 602, or the issuer (i) 604. A Point of Interaction (POI) can be a physical or virtual communication vehicle that provides the opportunity, through any channel to engage with the consumer for the purposes of providing content, messaging or other communication, related directly or indirectly to the facilitation or execution of a transaction between the merchant (m) 610 and the consumer. Examples of the POI include: a physical or virtual Point of Service (POS) terminal, the PCD of the consumer, a portable digital assistant, a cellular telephone, paper mail, e-mail, an Internet website rendered via a browser executing on computing device, or a combination of the forgoing. Thus, the POI terminal is in operative communication with the transaction processing system 600.

The PCD may interface with the POI using a mechanism including any suitable electrical, magnetic, or optical interfacing system such as a contactless system using radio frequency, a magnetic field recognition system, or a contact system such as a magnetic stripe reader. To illustrate, the POI may have a magnetic stripe reader that makes contact with the magnetic stripe of a healthcare card (e.g., Flexible Savings Account card) of the consumer. As such, data encoded in the magnetic stripe on the healthcare card of consumer read and passed to the POI at merchant (m) 610. These data can include an account identifier of a healthcare account. In another example, the POI may be the PCD of the consumer, such as the cellular telephone of the consumer, where the merchant (m) 610, or an agent thereof, receives the account identifier of the consumer via a webpage of an interactive website rendered by a browser executing on a World Wide Web (Web) enabled PCD.

Typically, a transaction begins with account user (au) 608 presenting the portable consumer device to the merchant (m) 610 to initiate an exchange for resources (e.g., a good or service). The portable consumer device may be associated with an account (e.g., a credit account) of account holder (a) 608 that was issued to the account holder (a) 608 by issuer (i) 604.

Merchant (m) 610 may use the POI terminal to obtain account information, such as a number of the account of the account holder (a) 608, from the portable consumer device. The portable consumer device may interface with the POI terminal using a mechanism including any suitable electrical, magnetic, or optical interfacing system such as a contactless system using radio frequency or magnetic field recognition system or contact system such as a magnetic stripe reader. The POI terminal sends a transaction authorization request to the issuer (i) 604 of the account associated with the PCD. Alternatively, or in combination, the PCD may communicate with issuer (i) 604, transaction handler (th) 602, or acquirer (a) 606.

Issuer (i) 604 may authorize the transaction and forward same to the transaction handler (th) 602. Transaction handler (th) 602 may also clear the transaction. Authorization includes issuer (i) 604, or transaction handler (th) 602 on behalf of issuer (i) 604, authorizing the transaction in connection with issuer (i) 604's instructions such as through the use of business rules. The business rules could include instructions or guidelines from the transaction handler (th) 602, the account holder (a) 608, the merchant (m) 610, the acquirer (a) 606, the issuer (i) 604, a related financial institution, or combinations thereof. The transaction handler (th) 602 may, but need not, maintain a log or history of authorized transactions. Once approved, the merchant (m) 610 may record the authorization, allowing the account user (au) 608 to receive the good or service from merchant (m) or an agent thereof.

The merchant (m) 610 may, at discrete periods, such as the end of the day, submit a list of authorized transactions to the acquirer (a) 606 or other transaction related data for processing through the transaction processing system 600. The transaction handler (th) 602 may optionally compare the submitted authorized transaction list with its own log of authorized transactions. The transaction handler (th) 602 may route authorization transaction amount requests from the corresponding the acquirer (a) 606 to the corresponding issuer (i) 604 involved in each transaction. Once the acquirer (a) 606 receives the payment of the authorized transaction from the issuer (i) 604, the acquirer (a) 606 can forward the payment to the merchant (m) 610 less any transaction costs, such as fees for the processing of the transaction. If the transaction involves a debit or pre-paid card, the acquirer (a) 606 may choose not to wait for the issuer (i) 604 to forward the payment prior to paying merchant (m) 610.

There may be intermittent steps in the foregoing process, some of which may occur simultaneously. For example, the acquirer (a) 606 can initiate the clearing and settling process, which can result in payment to the acquirer (a) 606 for the amount of the transaction. The acquirer (a) 606 may request from the transaction handler (th) 602 that the transaction be cleared and settled. Clearing includes the exchange of financial information between the issuer (i) 604 and the acquirer (a) 606 and settlement includes the exchange of funds. The transaction handler (th) 602 can provide services in connection with settlement of the transaction. The settlement of a transaction includes depositing an amount of the transaction settlement from a settlement house, such as a settlement bank, which transaction handler (th) 602 typically chooses, into a clearinghouse bank, such as a clearing bank, that acquirer (a) 606 typically chooses. The issuer (i) 604 deposits the same from a clearinghouse bank, such as a clearing bank, which the issuer (i) 604 typically chooses, into the settlement house. Thus, a typical transaction involves various entities to request, authorize, and fulfill processing the transaction.

The transaction processing system 600 will preferably have network components suitable for scaling the number and data payload size of transactions that can be authorized, cleared and settled in both real time and batch processing. These include hardware, software, data elements, and storage network devices for the same. Examples of transaction processing system 600 include those operated, at least in part, by: AMERICAN EXPRESS® Travel Related Services Company, Inc; Mastercard® International, Inc.; DISCOVER® Financial Services, Inc.; FIRST DATA® Corporation; DINERS CLUB INTERNATIONAL®, LTD; VISA® Inc.; and agents of the foregoing.

Each of the network/switch (ns) 602 can include one or more data centers for processing transactions, where each transaction can include up to 100 kilobytes of data or more. The data corresponding to the transaction can include information about the types and quantities of goods and services in the transaction, information about the account holder (a) 608, the account user (au) 608, the merchant (m) 610, tax and incentive treatment(s) of the goods and services, coupons, rebates, rewards, loyalty, discounts, returns, exchanges, cash-back transactions, etc.

By way of example, network/switch (ns) 602 can include one or more mainframe computers (e.g., one or more IBM® mainframe computers) for one or more server farms (e.g., one or more SUN® UNIX® Super servers), where the mainframe computers and server farms can be in diverse geographic locations.

Each issuer (i) 604 (or agent issuer (ai) 604 thereof) and each acquirer (a) 606 (or agent acquirer (aq) 606 thereof) can use or more router/switch (e.g., CISCO® routers/switches) to communicate with each network/switch (ns) 602 via dedicated communication systems.

Transaction handler (th) 602 can store information about transactions processed through transaction processing system 600 in data warehouses such as may be incorporated as part of the plurality of networks/switches 602. This information can be data mined. The data mining transaction research and modeling can be used for advertising, account holder and merchant loyalty incentives and rewards, fraud detection and prediction, and to develop tools to demonstrate savings and efficiencies made possible by use of the transaction processing system 600 over paying and being paid by cash, or other traditional payment mechanisms.

FIG. 6 includes transaction handler (th) 602 communicating through access points 630, 632 with acquirers 606, and issuers 604. Other entities such as drawee banks and third party authorizing agents may also connect to the network through access points 630, 632. Access points 630, 632 are typically made up of small computer systems located at a processing center that interfaces between the center's host computer and an interchange center. The access point facilitates the transmission of messages and files between the host and the interchange center supporting the authorization, clearing and settlement of transaction. Telecommunication links between the acquirer (q) 606 and its access point 632, and between the access point 630 and issuer (i) 604, are typically local links within a center and use a proprietary message format as preferred by the center.

As mentioned above, access points 630, 632 are typically located at a data processing center that interfaces between the data processing center's host computer and an interchange center. The interchange center is a data processing center that may be located anywhere in the world. In one implementation, there are two in the United States and one each in the United Kingdom and in Japan. Each interchange center houses the computer system that performs the network transaction processing. The interchange center serves as the control point for the telecommunication facilities of the network, which comprise high speed leased lines or satellite connections based on IBM® SNA protocol. Preferable, the communication lines that connect an interchange center (Transaction Handler 402) to remote entities use dedicated high-bandwidth telephone circuits or satellite connections based on the IBM® SNA-LUO communication protocol. Messages are sent over these lines using any suitable implementation of the ISO 8583 standard.

A data processing center (such as is located within an acquirer, issuer, or other entity) houses processing systems that support merchant and business locations and maintains customer data and billing systems. Preferably, each data processing center is linked to one or two interchange centers. Processors are connected to the closest interchange, and if the network experiences interruptions, the network automatically routes transactions to a secondary interchange center. Each interchange center is also linked to all of the other interchange centers. This linking enables processing centers to communicate with each other through one or more interchange centers. Also, processing centers can access the networks of other programs through the interchange center. Further, the network ensures that all links have multiple backups. The connection from one point of the network to another is not usually a fixed link; instead, the interchange center chooses the best possible path at the time of any given transmission. Rerouting around any faulty link occurs automatically.

The VisaNet® system is an example component of the transaction handler (th) 602 in the transaction processing system 600. Presently, the VisaNet® system is operated in part by Visa Inc. As of 2006, the VisaNet® system Inc. was processing around 300 million transaction daily, on over 1 billion accounts used in over 170 countries. Financial instructions numbering over 16,000 connected through the VisaNet® system to around 30 million merchants (m) 610. In 2007, around 81 billion transactions for about 4 trillion U.S. dollars were cleared and settled through the VisaNet® system, some of which involved a communication length of around 24,000 miles in around two (2) seconds and during which a plurality of stops are made for processing data in the transaction.

The steps, methods, processes, and devices described in connection with the implementations disclosed herein, are made with reference to the Figures, in which like numerals represent the same or similar elements. While described in terms of the best mode, it will be appreciated by those skilled in the art that the description is intended to cover alternatives, modifications, and equivalents as may be included within the spirit and scope of the invention as defined by the appended claims and their equivalents as supported by the following disclosure and drawings. Reference throughout this specification to "one implementation," "an implementation," or similar language means that a particular feature, structure, or characteristic described in connection with the implementation is included in at least one implementation of the present invention. Thus, appearances of the phrases "in one implementation," "in an implementation," and similar language throughout this specification may, but do not necessarily, all refer to the same implementation.

The described features, structures, or characteristics of the invention may be combined in any suitable manner in one or more implementations. In the following description, numerous specific details are recited to provide a thorough understanding of implementations of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow charts included are generally set forth as logical flow chart diagrams. As such, the depicted order and labeled steps are indicative of one implementation of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention may be embodied in other specific forms without departing from its spirit or essential characteristics. The described implementations are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method comprising:
  receiving, at a server computer, through an acquirer and from a Point-of-Sale (POS) terminal associated with a healthcare provider, an authorization request message which requests authorization to conduct a transaction on an account for the sale of a service of an administering of an influenza vaccine after a bearer of a prepaid card associated with the account and comprising a computer readable memory storing data including an identifier for an influenza vaccine and an identifier associated with the account causes the Point-of-Sale terminal to read the data from the prepaid card,
  wherein the authorization request message includes the identifier for the influenza vaccine and the identifier for the account, and wherein the identity of the bearer of the prepaid card is anonymous by not encoding data sufficient to identify the bearer of the prepaid card on the prepaid card;
  determining, by the server computer, an issuer of the account based on the identifier for the account;
  routing, by the server computer, the authorization request message to the issuer of the account, wherein the issuer operates an issuer computer that is configured to:
    determine, using the identifier for the account and the identifier for the influenza vaccine that the transaction is authorized,
    deactivate the identifier associated with the account after the transaction is authorized such that further authorization request messages that include the identifier associated with the account will be declined, deactivate the prepaid card upon determining that there are no active identifiers associated with the account included in the prepaid card, generate an authorization response message indicating approval of the transaction, and transmit the authorization request message to the server computer;

receiving, at the server computer the authorization response message indicating approval of the transaction from the issuer;

sending, by the server computer, the authorization response message to the POS terminal, wherein after the receiving of the authorization response message, the healthcare provider thereafter administers the influenza vaccine; and clearing and settling, by the server computer, the transaction between the account associated with the prepaid card and an account associated with the healthcare provider.

2. The method as defined in claim 1, wherein the issuer determines that the transaction is authorized even when the account has an insufficient balance, whereby an amount associated with the transaction will be collected by the issuer from a third party after the transaction has been conducted between the bearer of the prepaid card and the healthcare provider.

3. The method as defined in claim 1, wherein the prepaid card comprises a magnetic strip and visual indicia on a surface of the prepaid card, the visual indicia indicating that the prepaid card is only used for the influenza vaccine.

4. A computer comprising:
a processor; and
a non-transient computer readable medium comprising instructions which, when executed by the processor, causes the processor to the method of claim 1.

5. The method of claim 1 wherein the prepaid card further includes a location of where the influenza vaccine can be obtained.

6. The method of claim 1 wherein the prepaid card further comprises an account identifier associated with the bearer for use on items other than the influenza vaccine.

7. The method of claim 1 wherein the computer readable memory further stores an expiration date of the prepaid card, an influenza vaccine type, and an influenza vaccine quantity.

8. The method of claim 1 wherein the server computer is in a transaction handler.

9. The method of claim 1 wherein the authorization request message comprises a cost of providing the influenza vaccine to the bearer of the prepaid card.

10. The method of claim 1 further comprising, entering, the cost of providing the influenza vaccine into the Point-of-Sale terminal by the healthcare provider.

11. The method of claim 1 wherein the prepaid card comprises indicia indicating that the prepaid card is for an influenza vaccine and indicates one of a nasal or injection mode of administration.

12. The method of claim 1 wherein the prepaid card is a single use prepaid card.

13. The method of claim 1 wherein the prepaid card includes one or more identifiers associated with the account and further comprising deactivating the prepaid card upon determining that all of the one or more identifiers associated with the account included on the prepaid card have been deactivated.

14. The method of claim 1 wherein the prepaid card is one of a plurality of prepaid cards associated with the account, each of which is issued to a different bearer of a plurality of bearers.

15. The method of claim 14 wherein the account is funded and maintained by a sponsor separate from the plurality of bearers.

16. A method comprising:
receiving, at a Point-of-Sale (POS) terminal associated with a healthcare provider, an identifier for an influenza vaccine and an identifier for an account by an issuer after a bearer of a prepaid card associated with the account and comprising a computer readable memory storing data including an identifier for an influenza vaccine and an identifier associated with the account causes the Point-of-Sale terminal to read the data from the prepaid card, and wherein the identity of the bearer of the prepaid card is anonymous by not encoding data sufficient to identify the bearer of the prepaid card on the prepaid card;

generating, by the POS terminal, an authorization request message including the identifier for the influenza vaccine and the identifier for the account;

sending the authorization request message to the issuer via an acquirer and a transaction handler, wherein the issuer thereafter determines, using the identifier for the account and the identifier for the influenza vaccine that the transaction is authorized, and subsequently deactivates the account identifier after the transaction is authorized such that further authorization request messages that include the account identifier will be declined, and wherein the issuer subsequently deactivates the prepaid card upon determining that there are no active account identifiers associated with the prepaid card;

receiving, at the POS terminal and from the issuer via the transaction handler and the acquirer, an authorization response message, wherein the healthcare provider thereafter administers the influenza vaccine.

17. The method as defined in claim 16, wherein the issuer authorizes the transaction on the account even when the account has an insufficient balance, whereby an amount associated with the transaction will be collected by the issuer from a third party after the transaction has been conducted.

18. The method as defined in claim 16 wherein the prepaid card comprises a magnetic strip and visual indicia on a surface of the prepaid card, the visual indicia indicating that the prepaid card is only used for the influenza vaccine.

19. A POS terminal comprising:
a processor; and
a non-transient computer readable medium comprising instructions which, when executed by the processor, causes the processor to perform the method of claim 16.

* * * * *